(12) United States Patent
Weimer

(10) Patent No.: US 6,399,317 B1
(45) Date of Patent: Jun. 4, 2002

(54) REAL TIME DETECTION OF ANTIGENS

(75) Inventor: Bart C. Weimer, Logan, UT (US)

(73) Assignee: Utah State University, North Logan, UT (US)

( * ) Notice: Subject to any disclaimer, the term of this patent is extended or adjusted under 35 U.S.C. 154(b) by 0 days.

(21) Appl. No.: 09/292,172

(22) Filed: Apr. 15, 1999

Related U.S. Application Data

(60) Provisional application No. 60/081,889, filed on Apr. 15, 1998.

(51) Int. Cl.[7] .................... G01N 33/53; G01N 33/567
(52) U.S. Cl. .................... 435/7.2; 435/7.4; 435/607.4; 435/180; 435/7.5; 435/2; 436/518; 210/198.2; 428/403
(58) Field of Search .................... 210/198.2; 435/607.4, 435/180, 7.21, 7.5, 2; 530/362; 424/9.52, 489; 428/403; 252/315, 408.1; 436/518

(56) References Cited

U.S. PATENT DOCUMENTS

| | | | |
|---|---|---|---|
| 3,947,352 A | | 3/1976 | Cuatrecasas et al. |
| 4,157,323 A | | 6/1979 | Yen et al. |
| 4,217,338 A | | 8/1980 | Quash |
| 4,225,487 A | | 9/1980 | Cuatrecasas et al. |
| 4,347,244 A | | 8/1982 | Mynard et al. |
| 4,352,884 A | * | 10/1982 | Nakashima et al. ........ 435/180 |
| 4,478,946 A | | 10/1984 | Van der Merwe et al. |
| 4,483,807 A | * | 11/1984 | Asano et al. .................. 264/22 |
| 4,652,518 A | | 3/1987 | Makela et al. |
| 4,732,811 A | * | 3/1988 | Margel ........................ 428/403 |
| 4,837,305 A | * | 6/1989 | Goodman et al. .......... 530/345 |
| 5,147,777 A | | 9/1992 | Sutton et al. |
| 5,192,551 A | | 3/1993 | Willoughby, Jr. et al. |
| 5,216,130 A | * | 6/1993 | Line et al. .................. 530/362 |
| 5,225,330 A | | 7/1993 | Ginsburg et al. |
| 5,240,602 A | * | 8/1993 | Hammen ................. 210/198.2 |
| 5,240,640 A | * | 8/1993 | Siiman et al. .............. 252/315 |
| 5,292,840 A | | 3/1994 | Heilmann et al. |
| 5,314,830 A | | 5/1994 | Anderson et al. |
| 5,395,754 A | * | 3/1995 | Lambotte et al. ........ 435/607.4 |
| 5,437,983 A | * | 8/1995 | Watts et al. .................. 435/7.5 |
| 5,466,609 A | * | 11/1995 | Siiman et al. ............... 436/518 |
| 5,501,863 A | * | 3/1996 | Rossling et al. ............ 424/489 |
| 5,512,659 A | | 4/1996 | Ullman et al. |
| 5,552,086 A | * | 9/1996 | Siiman et al. ........... 252/408.1 |
| 5,620,858 A | | 4/1997 | Armstrong et al. |
| 5,627,233 A | * | 5/1997 | Hubbell et al. ............. 525/54.1 |
| 5,637,576 A | | 6/1997 | Heerze et al. |
| 5,639,620 A | * | 6/1997 | Siiman et al. .............. 435/7.21 |
| 5,665,561 A | | 9/1997 | Tuomanen et al. |
| 5,665,582 A | | 9/1997 | Kausch et al. |
| 5,707,877 A | * | 1/1998 | Siiman et al. ............... 436/518 |
| 5,713,943 A | * | 2/1998 | Lindgren ..................... 607/116 |
| 5,721,109 A | | 2/1998 | Yano et al. |
| 5,776,706 A | * | 7/1998 | Siiman et al. .............. 435/7.21 |
| 5,843,633 A | * | 12/1998 | Yin et al. ........................ 435/2 |
| 5,858,534 A | | 1/1999 | Sucholeiki |
| 5,858,802 A | | 1/1999 | Chai-Gao et al. |
| 6,193,953 B1 | * | 2/2001 | Lohrmann et al. ......... 424/9.52 |

FOREIGN PATENT DOCUMENTS

| | | | | |
|---|---|---|---|---|
| EP | 0382215 | * | 2/1989 | |
| EP | 170697 | * | 10/1991 | A61K/39/44 |

OTHER PUBLICATIONS

Manca, F et al, European Journal of Immunology, vol. 26(10), pp. 2461–2469, (Abstract only), Oct. 1996.*

Blake, MR et al, Applied and Environmental Microbiology, vol. 63(5), pp. 1643–1646, May 1997.*

Food Safety: Magnetic Beads Detect Spores. Food Ingredient News, vol. 5(6), Jun. 1, 1997, ISSN: 1070–1788,*

* cited by examiner

Primary Examiner—Lynette R. F. Smith
Assistant Examiner—Ginny Allen Portner
(74) Attorney, Agent, or Firm—Clayton, Howarth & Cannon, P.C.

(57) ABSTRACT

A modified bead having a structure represented by the formula B—X—A is disclosed, wherein B is a solid support preferably in the form of a bead, X is a spacer selected from the group consisting of poly(threonine), poly(serine), dextran, and poly(ethylene glycol), and A is an antibody. Using such modified beads in an immunoflow module, antigens can be captured and detected from food and environmental samples in about 30 minutes.

4 Claims, 6 Drawing Sheets

Concentration of B. stearothermophilus Spores in Sample (cfu/ml)

REAL TIME DETECTION OF ANTIGENS

CROSS-REFERENCE TO RELATED APPLICATIONS

This application claims the benefit of U.S. Provisional Application No. 60/081,889, filed Apr. 15, 1998, which is hereby incorporated herein by reference.

BACKGROUND OF THE INVENTION

This invention relates to detection of antigens. More particularly, the invention relates to compositions and methods for detection of selected antigens in real time. In a preferred embodiment, the invention relates to compositions and processes for sensitive detection of microbes and contaminants in food samples, environmental samples, and the like within about 30 minutes.

Considerable progress in the development of biosensors for microbial detection has been achieved in the last decade. These biosensors can be applied to medical, process control, and environmental fields. They must possess ideal features such as high specificity, simplicity, sensitivity, reliability, reproducibility, and speed. S. Y. Rabbany et al., Optical Immunosensors, 22 Crit. Rev. Biomed. Engin. 307–346 (1994). With the use of antibodies as the recognition element for specific capture, numerous applications have been developed for detection of pathogenic bacteria. M. R. Blake & B. C. Weimer, Immunomagnetic Detection of *Bacillus stearothermophilus* Spores in Food and Environmental Samples, 63 J. Appl. Environ. Microbiol. 1643–1646 (1997); A. Burkowski, Rapid Detection of Bacterial Surface Proteins Using an Enzyme-linked Immunosorbent Assay System, 34 J. Biochem. Biophys. Methods 69–71 (1997); S. A. Chen et al., A Rapid, Sensitive and Automated Method for Detection of Salmonella Species in Foods Using AG-9600 AmpliSensor Analyzer, 83 J. Appl. Microbiol. 314–321 (1997); L. A. Metherell et al., Rapid, Sensitive, Microbial Detection by Gene Amplification using Restriction Endonuclease Target Sequence, 11 Mol. Cell Probes 297–308 (1997); F. Roth et al., A New Multiantigen Immunoassay for the Quantification of IgG Antibodies to Capsular Polysaccharides of *Streptococcus pneumoniae*, 176 J. Inf. Dis. 526–529 (1997).

Bacterial spores are the most heat-stable form of microorganisms, are ubiquitous in the environment, and are therefore of great concern in food products (e.g., milk) that receive extensive heat treatments to prolong shelf life. Spore counts in milk from around the world vary between zero and >22,000 cfu/ml depending on the climate of the region. S. A. Chen et al., A Rapid, Sensitive and Automated Method for Detection of Salmonella Species in Foods using AG-9600 AmpliSensor Analyzer, 83 J. Appl. Microbiol. 314–321 (1997). *Bacillus stearothermophilus* spores are one of the most heat-resistant bacterial spores and are found in high numbers in soil and water. Contaminating *B. stearothermophilus* spores survive extreme heat to germinate and grow at elevated product storage temperatures, which occur in foods transported in equatorial regions of the world.

While *B. stearothermophilus* is not commonly a problem, other bacilli often lead to food-borne illness or spoilage in a variety of foods. *Bacillus cereus, Bacillus licheniformis, Bacillus subtilis,* and *Bacillus pumilus* have all been implicated in outbreaks of food-borne illness and are commonly isolated from raw and heat treated milk (M. W. Griffiths, Foodborne Illness Caused by Bacillus spp. other than *B. cereus* and Their Importance to the Dairy Industry, 302 Int. Dairy Fed. Bulletin 3–6 (1995)). *B. cereus* is also responsible for a sweet curdling defect in milk as well as being pathogenic. W. W. Overcast & K. Atmaram, . 1973. The Role of *Bacillus cereus* in Sweet Curdling of Fluid Milk, 37 J. Milk Food Technol. 233–236 (1973). A mesophilic heat resistant bacillus similar to *Bacillus badius,* has been isolated from extreme temperature processed milk ($D_{147}$=5 sec; P. Hammer et al., Pathogenicity Testing of Unknown Mesophilic Heat Resistant Bacilli from UHT-milk, 302 Int. Dairy Fed. Bulletin 56–57 (1995)). *B. badius* is a mesophilic organism and grows readily at room temperature, making it a likely candidate for spoiling temperature-processed foods. There have been 52 confirmed cases of *B. badius* in UHT milk in Europe and two cases outside of Europe (P. Hammer et al., supra). Lack of a rapid spore assay that can be used in milk contributes to the difficulty of prediction of post processing spoilage, thereby limiting the shelf life and product safety (H. Hofstra et al., Microbes in Food-processing Technology, 15 FEMS Microbiol. Rev. 175–183 (1994)). Such an assay could be used in a hazard analysis critical control point (HACCP) plan allowing raw materials with high spore loads to be diverted to products that do not pose a food safety risk to consumers.

The standard method for quantifying spores in milk, G. H. Richardson, Standard Methods for the Examination of Dairy Products (1985), involves heat-shocking and an overnight plate count. This is time-consuming and yields historical information. The food industry needs microbiological assays to yield predictive information for maximum benefit in HACCP analysis and risk assessment. An enyzme-linked immunosorbent assay (ELISA) capable of detecting $>10^6$ cfu/ml of *B. cereus* spores in foods has been reported, but was unacceptable due to antibody cross-reactivity (Y. H. Chang & P. M. Foegeding, Biotin-avidin Enzyme-linked Immunosorbent Assay for Bacillus Spores in Buffer and Food, 2 J. Rapid Methods and Autom. Microbiol. 219–227 (1993)).

Techniques to increase sensitivity of immunosorbent assays have focused on more efficient reporter labels, such as faster catalyzing reporter-enzymes; signal amplification, such as avidin- or streptavidin-biotin enzyme complexes; and better detectors, such as luminescence and fluorescence (L. J. Kricka, Selected Strategies for Improving Sensitivity and Reliability of Immunoassays, 40 Clin. Chem. 347–357 (1994); P. Patel, Rapid Analysis Techniques in Food Microbiology (1994)). Immunomagnetic antigen capture is used extensively to separate and identify *Escherichia coli* and Salmonella from foods (C. Blackburn et al., Separation and Detection of Salmonellae Using Immunomagnetic Particles, 5 Biofouling 143–156 (1991); P. M. Fratamico et al., Rapid Isolation of *Escherichia coli* O0157:H7 from Enrichment Cultures of Foods Using an Immunomagnetic Separation Method, 9 Food Microbiol. 105–113 (1992); L. Krusell & N. Skovgaard, Evaluation of a New Semi-automated Screening Method for the Detection of Salmonella in Foods within 24 h, 20 Inter. J. Food Microbiol. 124–130 (1993); A. Lund et al., Rapid Isolation of K88+*Escherichia coli* by Using Immunomagnetic Particles, 26 J. Clin. Microbiol. 2572–2575 (1988); L. P. Mansfeild & S. J. Forsythe, Immunomagnetic Separation as an Alternative to Enrichment Broths for Salmonella Detection, 16 Letters Appl. Microbiol. 122–125 (1993); A. J. G. Okrend et al., Isolation of *Escherichia coli* O157:H7 Using O157 Specific Antibody Coated Magnetic Beads, 55 J. Food Prot. 214–217 (1992); E. Skjerve & Olsvic, Immunomagnetic Separation of Salmonella from Foods, 14 Inter. J. Food Microbiol. 11–18 (1991); D. J. Wright et al., Immunomagnetic Separation as a Sensitive Method for Isolating *Escherichia coli* O157 from Food Samples, 113 Epidemiol. Infect. 31–39 (1994)).

However, these methods involve either a preincubation or a subsequent incubation step (usually 18 to 24 h) to increase the cell numbers for detection. Immunomagnetic capture greatly shortens *E. coli* and Salmonella testing, but long incubation times limit this method for predictive information. Immunocapture has also been used to quantitate *Bacillus anthracis* spores in soil samples using luminescent detection (J. G. Bruno & H. Yu, Immunomagnetic-electrochemiluminescent Detection of *Bacillus anthracis* Spores in Soil Matrices, 62 App. Environ. Microbiol. 3474–3476 (1996)), but these efforts have led to tests that have a detection limit of $10^3$ cfu/ml.

In view of the foregoing, it will be appreciated that compositions and methods for real time detection of selected antigens, such as contaminants in food and the environment, would be a significant advancement in the art.

BRIEF SUMMARY OF THE INVENTION

It is an object of the present invention to provide a method for rapid detection of antigens.

It is another object of the invention to provide a method for rapid and sensitive capture of antigens from a fluid.

It is also an object of the invention to compositions for capture and detection of antigens in real time.

These and other objects can be addressed by providing a composition represented by the formula B—X—A, wherein B is a solid substrate in the form of a bead, A is an antibody, and X is a spacer selected from the group consisting of poly(threonine), poly(serine), poly(ethylene glycol), and dextran. Preferably, the bead is composed of a material selected from the group consisting of glass, silicon, silica, quartz, metal oxides (ceramics), and organic polymers, such as poly(vinyl alcohol), polystyrene, and poly(acrylic acid), and the like. Glass and ceramics are especially preferred. It is also preferred that the bead have a diameter in the range of about 1 to 7 mm. In preferred embodiments, the antibody has a specific affinity for binding a microorganism or propagule thereof, such as a spore.

Another aspect of the invention comprises an apparatus for use in capturing antigens comprising:

(a) a housing, defining a chamber; comprising an inlet opening for conducting a fluid into the chamber and an outlet opening for conducting the fluid out of the chamber;

(b) a plurality of compositions represented by the formula B—X—A, wherein B is a solid substrate in the form of a bead, A is an antibody, and X is a spacer selected from the group consisting of poly(threonine), poly(serine), poly(ethylene glycol), and dextran, wherein the plurality of compositions are disposed in the chamber; and (c) a plate having a plurality of holes formed therein, wherein the plate is disposed in the chamber such that the fluid flows through the plurality of holes after being conducted into the chamber and before being conducted out of the chamber and wherein each of the plurality of holes is sized such that the plurality of compositions is retained in the chamber when the fluid flows therethrough.

Still another aspect of the invention comprises a method of capturing an antigen contained in a fluid comprising:

(a) providing a composition represented by the formula B—X—A, wherein B is a solid substrate in the form of a bead, A is an antibody, and X is a spacer selected from the group consisting of poly(threonine), poly(serine), poly(ethylene glycol), and dextran; and (b) causing the fluid to flow over the composition such that the antigen contacts the antibody and is bound thereto.

Preferably, the fluid flows over the composition at a rate of about 1 to 120 liters per minute. It is also preferred that the fluid is caused to flow over the composition in a fluidized bed reactor.

Yet another aspect of the invention comprises a method of detecting an antigen contained in a fluid comprising:

(a) providing a composition represented by the formula B—X—A, wherein B is a solid substrate in the form of a bead, A is an antibody, and X is a spacer selected from the group consisting of poly(threonine), poly(serine), poly(ethylene glycol), and dextran; and (b) causing the fluid to flow over the composition such that the antigen contacts the antibody and is bound thereto, forming a complex; and (c) detecting the complex and thereby detecting the antigen.

DETAILED DESCRIPTION

Figure 1A:
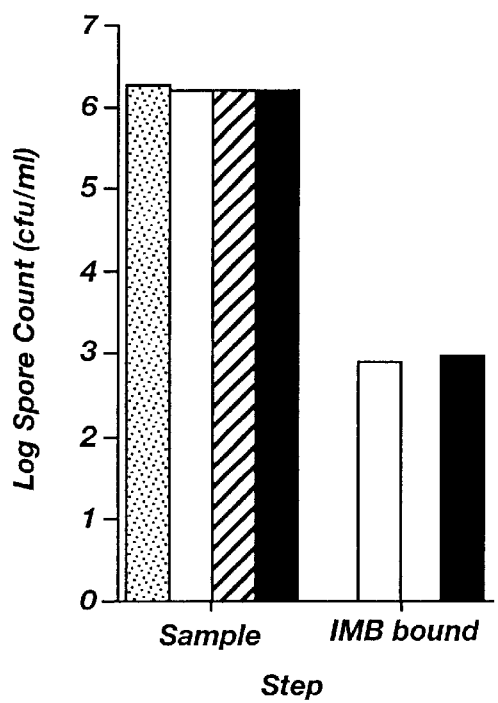
FIG. 1A illustrates specific capture of *B. stearothermophilus* spores from a mixed population containing equal amounts of *B. stearothermophilus* and *B. subtilis* spores, where *B. subtilis* spore counts in PBST are represented by the dotted bar, *B. stearothermophilus* spore counts in PBST are represented by the open bar, *B. subtilis* spore counts in milk are represented by the hatched bar, and *B. stearothermophilus* spore counts in milk are represented by the solid bar.

Before the present compositions and methods for detection of antigens are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. For example, reference to an apparatus containing "a bead" includes reference to two or more of such beads, reference to "a spacer" includes reference to one or more of such spacers, and reference to "an antibody" includes reference to two or more of such antibodies.

In describing and claiming the present invention, the following terminology will be used in accordance with the definitions set out herein.

As used herein, "cfu" means colony forming units.

As used herein, "PBS" means phosphate buffered saline: 0.01 M $Na_2HPO_4$, 0.15 M NaCl, pH 7.2.

As used herein, "PBST" means phosphate buffered saline containing 0.1% Tween 20.

As used herein, "BSA" means bovine serum albumin

A fluidized or extended volume reactor filled with beads that have been modified with antibodies was developed for capturing antigens, such as specific microorganisms and biological molecules, at flow rates varying from 1 to 120 L/min. The goal was to achieve sensitive real time detection without pre-incubation of samples before quantitation. To demonstrate the concept of bacterial capture, *Bacillus globigii* and *Bacillus stearothermophilus* spores were used at various concentrations. Capture of biological molecules was simulated with penicillin and bovine serum albumin (BSA). Additionally, unique monoclonal and polyclonal antibodies were developed against *B. stearothermophilus* ATCC 10149, *B. cereus* ATCC 11778, and *B. subtilis* 6633, and demonstrated to react specifically with the spores used to produce the antibodies. These antibodies were characterized for the influence of pH, temperature, ionic strength, coliform bacteria, and fat content on the ability to capture the microbe in a factorial design.

The influence of bead type (size and material), surface chemistry (crosslinker and spacer), sample type, and volumetric flow rate were investigated as parameters that influence the detection time and sensitivity. The bead type and size influenced the module configuration, and therefore the detection time and sensitivity. Use of either ceramic or glass 1–7 mm beads in a fluidized or extended bed configuration allowed single cell detection in real time for all microbes tested. Use of 2.8 $\mu$m immunomagnetic beads did not.

The surface chemistry configuration to capture all microbes tested controlled the ability of the antibodies to capture the microbe targets, but played no role in the capture of BSA. The common method known in the art for capturing a microbe on a solid phase with antibodies is to use a heterobifunctional cross linker that directionally orients the antibodies for capture of the antigen. Use of known methods, however, did not allow capture of the bacterial targets used in the present study. Hence, another molecule was used between the crosslinker and the antibody, which allowed spore capture. Only specific molecules were found to be useful including, but not limited to, polythreonine (PolyThr), polyserine (PolySer), dextran, and polyethylene glycol (PEG).

Sample type was investigated to determine if the complex matrix found in different environments influenced target binding. All samples tested allowed single cell detection within 30 min. This was predicted by the results from the factorial experiment that demonstrated that the main effects had no influence on binding in phosphate buffer. The detection of *B. globigii* in raw sewage demonstrated the predictive value of the laboratory experiment. Additionally, other foods were used to detect single cell amounts of the microbe targets.

Target capture in static and flow conditions was tested to determine the influence on the total test time and sensitivity. Static capture with immunomagnetic beads allowed a test time of 1.5–2.5 h with a detection limit of $10^3$ cfu/ml. Use of immunoflow capture (>1 L/min) allowed a detection time of no more than 30 min and detection limit of one cell. The detection limit for penicillin was at least 2 ppb, and that of BSA was found to be at least 0.075 ng/ml without signal amplification.

EXAMPLE 1

Bacteria

The bacteria used in the experiments described herein are described in Table 1. Commercial preparations of spores of *B. stearothermophilus* ATCC 10149, *B. cereus* ATCC 11778, and *B. subtilis* 6633 were purchased from Fisher Scientific, Pittsburgh, Pa. Viable spore numbers and germination estimates were obtained by plating on plate count agar (PCA) overnight at 65° C. and 30° C., respectively. All other spores except for *B. globigii* spores (Table 1) were prepared by spread-plating a single colony isolate on PCA and incubating the covered plate at 30° C. for approximately 2 weeks. Spores were swabbed from the surface of the agar and washed repeatedly in distilled water to remove water-soluble components. Spores were pelleted and separated from cell debris by centrifugation (1,500×g for 20 min at 4° C.; D. E. Gombas & R. F. Gomez, Sensitization of *Clostridium perfringens* Spores to Heat by Gamma Radiation, 36 Appl. Environ. Microbiol. 403–407 (1987)). Presence of spores was confirmed by heating to 80° C. for 15 min and then plating on PCA (G. H. Richardson, supra). Presence of an exosporium on the spore was tested by phase contrast microscopy with crystal violet staining (C. Du & K. Nickerson, *Bacillus thuringiensis* HD-73 Spores Have Surface-localized Cry Ac Toxin: Physiological and Pathogenic Consequences, 62 Appl. Environ. Microbiol. 3722–3726 (1996)). Spore titers were estimated by plating spores on plate count agar (PCA) and incubating overnight at 37° C. Based on these experiments, it was estimated that $10^{11}$ spores have a mass of 1 g.

TABLE 1

| Species | Inc. temp. (° C.) | Source | Exosporium |
|---|---|---|---|
| *B. stearothermophilus* | 65 | ATCC 10149[a] | – |
| *B. cereus* | 30 | ATCC 11778[a] | + |
| *B. subtilis* | 30 | ATCC 6633[a] | + |
| *B. circulans* | 30 | ATCC 4513[b] | – |
| *B. coagulans* | 30 | ATCC 7050[b] | – |
| *B. globigii* | 30 | Dugway[c] | |
| *B. licheniformis* | 30 | OSU[d] | – |
| *B. mascerans* | 30 | OSU[d] | + |

TABLE 1-continued

| Species | Inc. temp. (° C.) | Source | Exosporium |
|---|---|---|---|
| B. polymyxa | 30 | ATCC 842[b] | + |
| B. pumilus | 30 | OSU[d] | − |

[a]Purchased from Fisher Scientific, Pittsburgh, Pennsylvania.
[b]Purchased from American Type Culture Collection.
[c]Obtained from Dugway Proving Grounds (Tooele, Utah).
[d]Donated by Floyd Bodyfelt, Oregon State University.

EXAMPLE 2

Polyclonal Antibodies Production

Polyclonal antibodies against B. cereus spores, B. subtilis spores, and B. stearothermophilus spores were made at the Utah State Biotechnology Center (Logan, Utah). BALB/c mice were injected in the intraperitoneal cavity with $1 \times 10^7$ cfu/ml cells or spores in sterile saline (0.5 ml) three times at 3-week intervals. E. Harlow & D. Lane, Antibodies, A Laboratory Manual (1988). Total ascites IgG was purified using a protein A/G column (Pierce Chemical, Rockford, Ill.). Antibodies were desalted and concentrated to 1 mg/ml in 0.1 M $NaPO_4$, pH 7.0 in a 30 kD Centricon filter (Amicon, Beverly, Mass.) at 4,500×g at 4° C.

Goat antibodies to Bacillus globigii spores were obtained from Dugway Proving Grounds (Tooele, Utah).

EXAMPLE 3

Monoclonal Antibody Production

Monoclonal antibodies were produced against B. stearothermophilus by suspending the cells or spores in PBS to an optical density of 0.93 at 550 nm before intraperitoneally injecting female BALB/c mice with 0.250 mg (whole cell wet weight) without adjuvant. The mice were immunized 3 times at 3-week intervals. Seven days after the last immunization they were test bled, and the serum was titered by ELISA 3 days before fusion. Booster injections were administered by intraperitoneal injection with 0.1 mg cells in PBS. Fusion with a compatible murine myeloma cell line (P3X63-Ag8.653) was done in the presence of polyethylene glycol. Selection for hybrid cells was done in HAT medium. G. Kohler & C. Milstein, Continuous Cultures of Fused Cells Secreting Antibody of Pre-defined Specificity, 256 Nature 495–97 (1975) (hereby incorporated by reference). Positive colonies were determined by ELISA, and subcloned twice before freezing in liquid nitrogen.

EXAMPLE 4

Antibody Specificity

Antibody specificity was tested by measuring the cross reactivity against Bacillus spores listed in Table 1 using a standard ELISA. A suspension of each spore type ($10^6$ cfu/ml), suspended in 50 mM $NaCO_3$ (pH 9.5), was nonspecifically bound to wells of a microtiter plate for 12 h at 4° C. Wells containing spores were blocked with 2% bovine serum albumin (BSA) in PBS for 4 h at 25° C., and washed four times with PBS containing 0.1% Tween 20 (PBST). Anti-B. stearothermophilus antibodies (1:10,000 serum dilution in PBS) were added to wells, slowly agitated for 2 h at 25° C., and washed four times with PBST. Horseradish-peroxidase-labeled (HRP) anti-whole mouse IgG (Sigma Chemical Co., St. Louis, Mo.) was added to label anti-B. stearothermophilus antibodies for 2 h, then the wells were washed four times with PBST. O-Phenylenediamine dihydrochloride (Sigma) color development was measured using a b* color scale (blue to yellow) at 37° C. for 1 h in an automated reflectance colorimeter (Omnispec 4000 Bioactivity monitor; Wescor, Inc., Logan, Utah).

The anti-B. stearothermophilus antibodies did not cross react with any of the spore types tested (Table 1) including common aerobic spores found in raw foods. Lack of cross reactivity may be partly due to the absence of an exosporium on the B. stearothermophilus spores (Table 1). However, antibodies raised against B. subtilis and B. cereus, which have exosporia, were also specific for the injected spore types, suggesting that the surface antigens of the exosporia are sufficiently different as to not crossreact.

EXAMPLE 5

Antibody Attachment to Beads via Biotin-streptavidin

Anti-B. stearothermophilus antibodies purified from total serum were biotinylated with NHS-LC-Biotin (Pierce Chemical, Rockford, Ill.). Efficiency of surface biotinylation was determined using the HABA assay (Pierce), except that the 2-mercaptoethanol step was omitted to avoid denaturing antibodies. This modified procedure gave the number of surface biotin moieties per antibody (Sigma Technical Support).

Biotinylated antibodies were coupled to streptavidin-bound magnetic beads (Dynabeads Streptavidin™, Lake Success, N.Y.) according to the supplier's directions.

EXAMPLE 6

Antibody Attachment to Bead Via Poly(threonine)

Sodium meta-periodate (5 mg) was used to oxidize carbohydrate moieties on the anti-B. stearothermophilus antibodies. G. T. Hermanson et al., Immobilized Affinity Ligand Techniques (1992) (hereby incorporated by reference). Sodium meta-periodate was removed after oxidation by washing five times with 0.1 M $NaPO_4$, pH 7.0, in a 30 kD Centricon filter (4,500×g, 4° C.), and the oxidized antibodies were then immediately crosslinked to beads magnetic beads.

PolyThr (MW(vis) 12,100; Sigma Chemical, St. Louis, Mo.) was covalently coupled to 2.8-$\mu$m, tosyl-activated polystyrene Dynabeads (Dynal, Lake Success, N.Y.) in 50 mM borate buffer (pH 9.5) via the terminal amine as described by the product instructions. Four washes (three times for 10 min, and once for 30 min) with TBS buffer (pH 7.5) were used to block remaining tosyl-active sites. Adenine dihydrazine (ADH; 0.5 M in 0.1 M MES, pH 4.75; Sigma) was linked to the carboxy terminus of the bound PolyThr using an ethylene diamine carbodiimide mediated reaction (G. T. Hermanson et al., supra). Oxidized antibodies were mixed with the ADH-activated beads at room temperature for 12 h to allow crosslinking between the oxidized carbohydrate moiety of the IgG and the ADH terminus of the PolyThr spacer (G. T. Hermanson et al., supra). After crosslinking, the modified immunomagnetic beads (IMBs) were stored rotating (50 rpm) in PBST with 0.02% sodium azide at 4° C. until use.

EXAMPLE 7

Antibody Attachment to Bead Via Poly(serine)

In this example, the procedure of Example 6 was followed except that poly(serine) was substituted for poly(threonine).

EXAMPLE 8

Antibody Attachment to Bead Via Dextran

Ceramic beads, 7 mm in diameter (Coors Ceramics Corp., Golden, Colo.), were washed in acidic methanol (HCl:methanol, 1:1) for 30 min at room temperature (RT) to strip the bead surface. The acidic methanol was poured off and the beads were rinsed several times with filtered water ($dH_2O$). The beads were further washed with concentrated sulfuric acid three times for 30 min, rinsed several times with $dH_2O$, and finally boiled in $dH_2O$ for 30 min to introduce hydroxyl groups onto the surface.

For silanization and crosslinking, beads were air dried, washed once in toluene and incubated in 3% 3-mercapto propyl trimethoxysilane (3% MTS in toluene) for 2 h at RT. Subsequently the beads were prepared for the addition of the crosslinker γ-maleimidobutyric acid N-hydroxy succinimide ester (GMBS; Sigma Chemicals, St. Louis, Mo.). Beads were washed twice in toluene to remove unbound MTS, air dried, and then incubated for 1 h at RT in 2 mM GMBS (in 100% ethanol). Finally, the beads were finally washed in 100% ethanol and then in PBS.

Dextran was used as a spacer between the crosslinker and the antibody. Sodium-m-periodate (Sigma Chemicals, St. Louis, Mo.) was used to oxidize the carbohydrate moieties on dextran (37.5 kDa, Sigma Chemicals, St. Louis, Mo.) for 3 h at RT while shaking. The salt was removed by washing four times with $dH_2O$ in 30 kDa Centricon filters (Amicon Inc., Beverly, Mass.) and immediately bound to the crosslinked beads. Adipic acid dihydride (ADH, 0.5 M in sodium phosphate, pH 7.2; Sigma Chemicals, St. Louis, Mo.) was then added to introduce an amine group to the bead surface, which could then react with the oxidized antibody. All unreacted sites were blocked with 1% Tris/BSA, pH 8.5.

EXAMPLE 9

In this example, anti-*B. stearothermophilus* antibodies were mixed with tosyl-activated magnetic beads (Dynal) according to the directions supplied with the beads such that the amine groups on the antibodies reacted with tosyl groups on the surface of the beads. The resulting modified beads contained the antibodies covalently bonded to the surface of the beads.

EXAMPLE 10

In this example, anti-Fc IgG was bound to magnetic beads according to the procedure of Example 9. After unbound IgG was washed off, the beads were reacted with anti-*B. stearothermophilus* antibodies such that the anti-Fc IgG bound the anti-*B. stearothermophilus* antibodies. The anti-Fc IgG thus formed a spacer between the magnetic beads and the anti-*B. stearothermophilus* antibodies.

EXAMPLE 11

In this example, anti-*B. stearothermophilus* antibodies attached to magnetic beads were tested for their ability to capture *B. stearothermophilus* spores. The antibody/bead conjugates (i.e., immunomagnetic beads or IMBs) were prepared according to the procedure of Examples 5, 6, 9, and 10. ELISA using HRP-labeled anti-IgG confirmed the presence of bound antibodies on the surfaces of the beads.

IMBs ($3 \times 10^6$ beads) were added to 1 ml of sample comprising $10^4$ or $10^6$ *B. stearothermophilus* spores in PBST. These mixtures were incubated for 30 min at 25° C. with rotation at 50 rpm. The IMBs were removed from the sample for 2 min with a magnetic particle concentrator (Dynal MPC-E-1) and washed four times with PBST to reduce IMB clumping and block spore adhesion to tube walls (E. Skjerve et al., Detection of *Listeria monocytogenes* in Foods by Immunomagnetic Separation, 56 Appl. Environ. Microbiol. 3478–3481 (1990)). After each wash, IMBs were transferred to a new microfuge tube. The presence of bound spores on IMBs was confirmed in duplicate by plate counts and phase contrast microscopy.

Table 2 shows the results of these experiments.

TABLE 2

| Attachment | Ab Modification | Ab Orientation | No. spores bound |
|---|---|---|---|
| Biotin-Streptavidin | NHS-LC-Biotinylation | Non-directional | $0^a$ $0^b$ |
| Ab-$NH_2$ to Tosyl groups on beads | None | Non-directional | $0^a$ $0^b$ |
| Anti-Fc IgG spacer | None | Directional | $0^a$ $0^b$ |
| PolyThr-ADH crosslinker | Carbohydrate oxidation | Directional | $160^a$ $3600^b$ |

$^a$Captured from $10^4$ spores/ml.
$^b$Captured from $10^6$ spores/ml.

These results show that of the conjugates tested only antibodies bound to beads through a poly(threonine) spacer were able to capture spores. These data suggest that spacer length and flexibility may play a role in the antibody-antigen interaction.

EXAMPLE 12

In this example, the procedure of Example 11 was followed except that conjugates containing poly(serine) (Example 7) and dextran (Example 8) spacers were substituted for the conjugate containing the poly(threonine) spacer. The results obtained with the poly(serine)- and dextran-containing conjugates were substantially similar to those obtained with the poly(threonine)-containing conjugate.

EXAMPLE 13

In this example, equal numbers of *B. subtilis* and *B. stearothermophilus* spores were mixed in PBST and in milk. Immunocapture using anti-*B. stearothermophilus* antibodies conjugated to magnetic beads was carried out according to the procedure of Example 11 except that samples containing milk were given 5 minutes to separate the beads from the medium using the magnetic particle concentrator due to the slower bead recovery. After capture of spores using the immunomagnetic bead conjugate, the conjugates were washed with PBST and the wash supernates were plated on PCA. This washing procedure was repeated three times such that a total of four wash supernates were assayed.

Figure 1B:
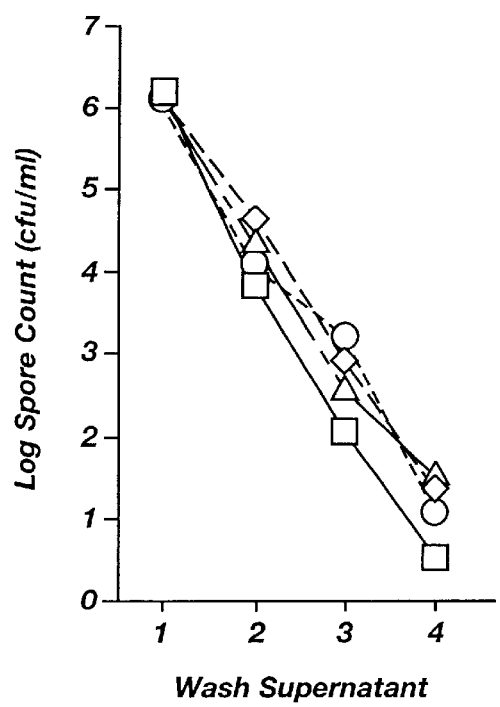
FIG. 1B shows the concentration of spores in the wash: (□) *B. subtilis* in PBST, (◇) *B. stearothermophilus* in PBST, (○) *B. subtilis* in milk, and (Δ) *B. stearothermophilus* in milk.

FIG. 1A shows the conjugate specifically captured *B. stearothermophilus* spores from PBST and milk containing equal numbers of *B. stearothermophilus* and *B. subtilis* spores. FIG. 1B shows that about 99% of non-specifically bound spores were removed from the conjugate with each wash, leaving *B. stearothermophilus* spores captured by the conjugate after four washes.

The anti-*B. stearothermophilus* antibodies did not cross react with any of the spore types tested (Table 1) including common aerobic spores found in raw foods.

EXAMPLE 14

Product Testing

In this example, muck clay, ground pepper, skim milk, whole milk, and acidic sandy soil were tested for detection of bacterial spores. Fluid products were tested with no modification. Powdered products were suspended at 1 g/ml. Anti-*B. stearothermophilus* antibody conjugated beads prepared according to the procedure of Example 6 were added to 1 ml of each product and mixed gently at 25° C. Bound spores were quantitated using colorimetric (as described above) or fluorescence detection. For fluorescence detection, spores bound to IMBs were labeled with secondary biotinylated anti-*B. stearothermophilus* antibodies. The IMBs were then washed with PBST and resuspended in an ABC-alkaline phosphatase complex solution (Vector Laboratories, Inc., Burlingame, Calif.) for 30 min. The IMBs were washed three times with PBST and resuspended in 100 μl of 0.2 M Tris buffer containing 0.1% BSA (pH 8.5) to remove unbound enzyme complex. A 40-μl suspension of the IMBs was added to 3 ml of Fluorophos substrate (Advanced Instruments, Norwood, Mass.) and fluorescence monitored for 2 min at 38° C. in a Fluorophos FLM200 fluorometer (Advanced Instruments, Norwood, Mass.).

Figure 2:
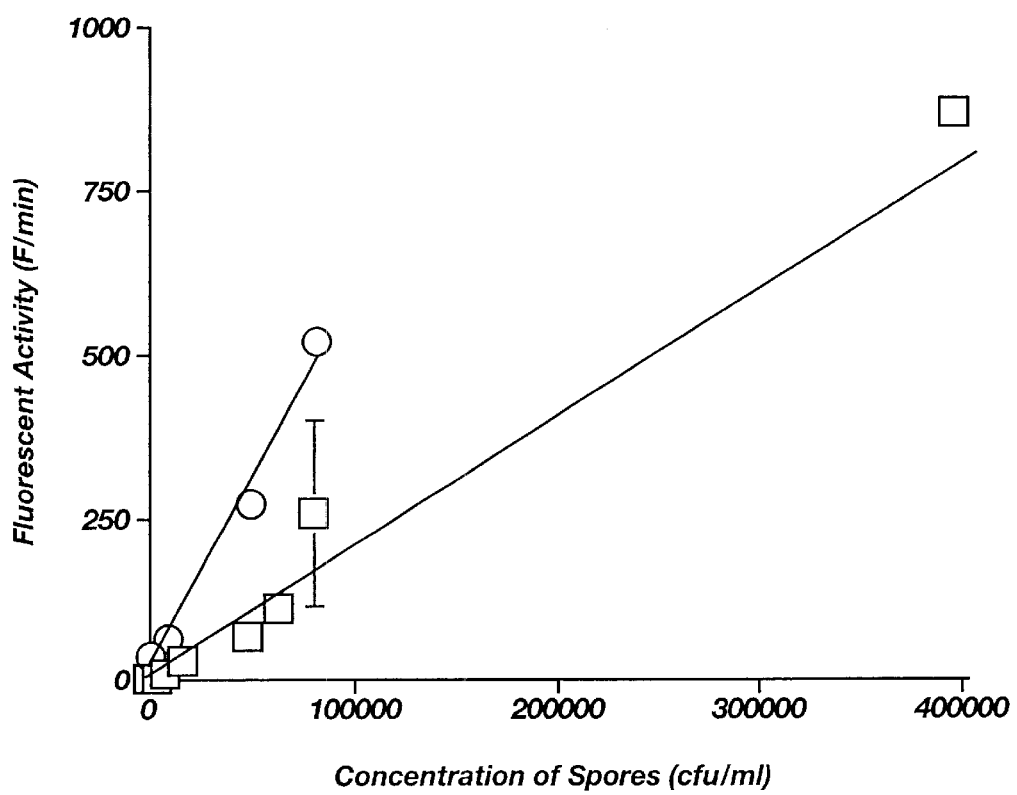
FIG. 2 shows fluorescence detection of captured *B. stearothermophilus* spores in skim milk by a biotin-avidin amplified sandwich ELISA using $3 \times 10^6$ (□) and $1.4 \times 10^7$ (○) immunomagnetic beads (IMBs); data points represent the mean of two replications, and error bars represent standard error of the means.

As shown in FIG. 2, using immunocapture-sandwich ELISA, spores in UHT skim milk were quantified down to $8 \times 10^3$ cfu/ml in 2 h with no pre-enrichment steps and no sample preparation. Increasing the number of beads in the assay increased the fluorescence activity, suggesting that this could further increase the assay sensitivity (P. M. Fratamico et al., supra; E. Skjerve et al., supra).

Figure 3:
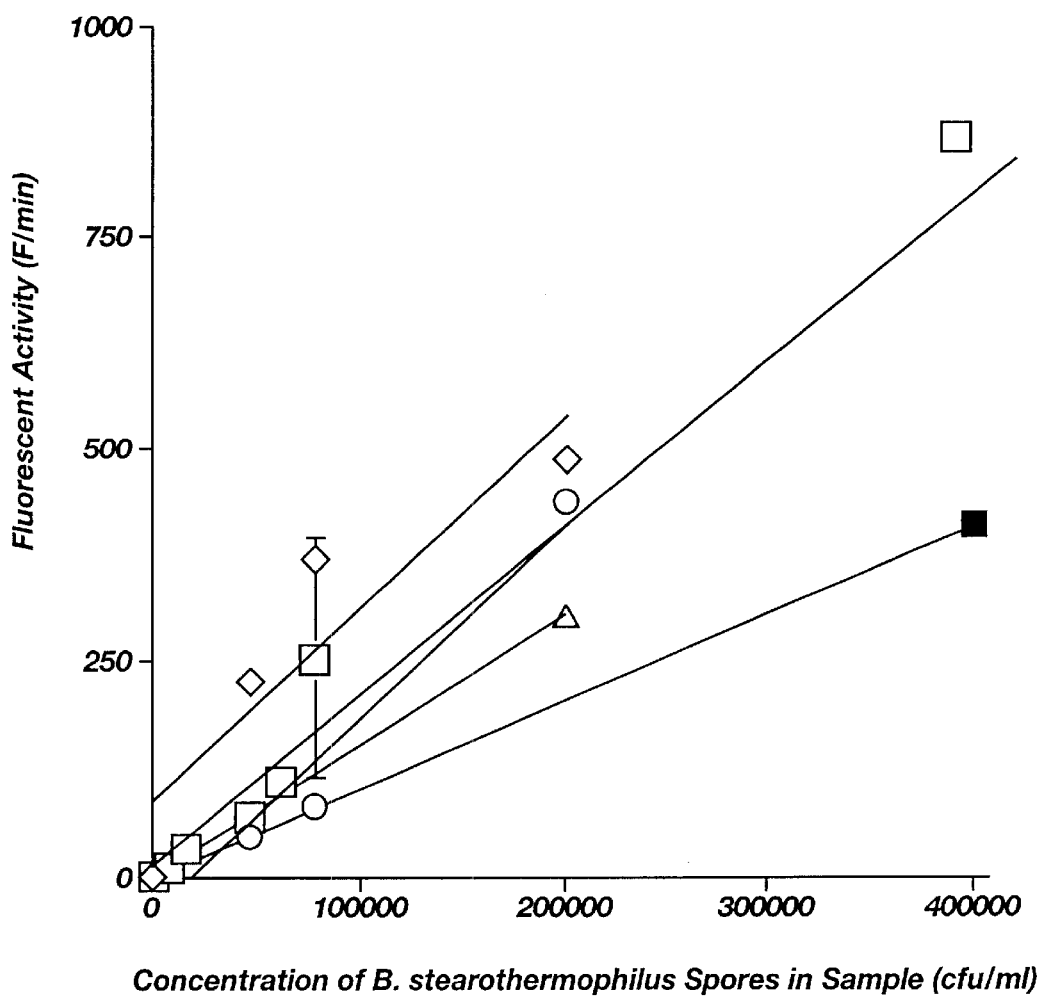
FIG. 3 shows fluorescence detection of captured *B. stearothermophilus* spores from various food and environmental samples using $3 \times 10^6$ IMBs: (◇) muck clay, $R^2 = 0.82$; (○) pepper, $R^2 = 0.96$; (■) skim milk, $R^2 = 0.99$; (Δ) whole milk; (■) acidic sandy soil (pH 3.7); data points represent the mean of two replications, and error bars represent standard error of the means.

The slope of the generated curves was similar for all samples tested, indicating that sample background did not grossly influence antigen binding (FIG. 3). Therefore, approximate spore loads can be obtained without calibrating the assay to each product. Foods containing fat, such as raw whole milk, required a longer time for separation of the IMBs and gentle removal of supernate to avoid trapping the beads in the fat and removing them with the supernate. Separation of IMBs from fatty products required 5 min rather than the 2 min used for nonfat samples. Soil samples containing a high percentage of iron fines interfered with bead recovery, although other soil types tested did not. These data support the use of this assay to test for *B. stearothermophilus* spores in food and environmental sample.

Since the assay has been designed to be used with raw ingredients that may vary in temperature, the ability of the IMBs to capture *B. stearothermophilus* spores at temperatures ranging from 4° C. to 55° C. was tested. IMBs were added to 1 ml UHT skim milk containing $5 \times 10^4$ *B. stearothermophilus* spores and incubated between 4° C. to 55° C. while rotating (50 rpm) for 30 min. The IMB were washed four times with PBST, plated on PCA, and incubated overnight at 65° C. *B. stearothermophilus* colonies were counted to quantitate bound spores. Regardless of the temperature of the sample, the number of spores captured from UHT skim milk containing $5 \times 10^4$ *B. stearothermophilus* spores did not vary significantly. This means that sample preparation time can be reduced. These data suggest that this approach is over 100 times more sensitive than the only other rapid spore assay (Y. H. Chang & P. M. Foegeding, supra), is about 10 times faster than any spore assay with equivalent sensitivity (G. H. Richardson, supra), and can be used to quantitate a single species of spore in a mixed spore population in chemically complex backgrounds.

Figure 4:
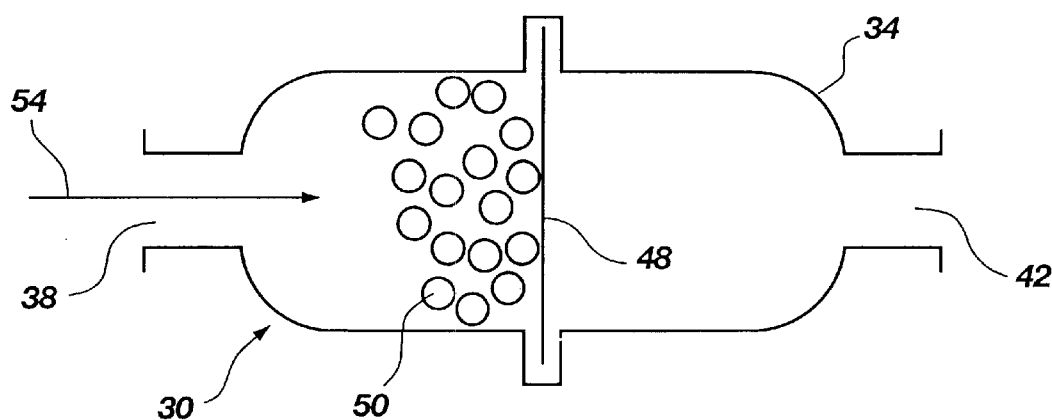
FIG. 4 shows a schematic representation of an illustrative module for use in detecting antigens according to the present invention.
Figure 5:
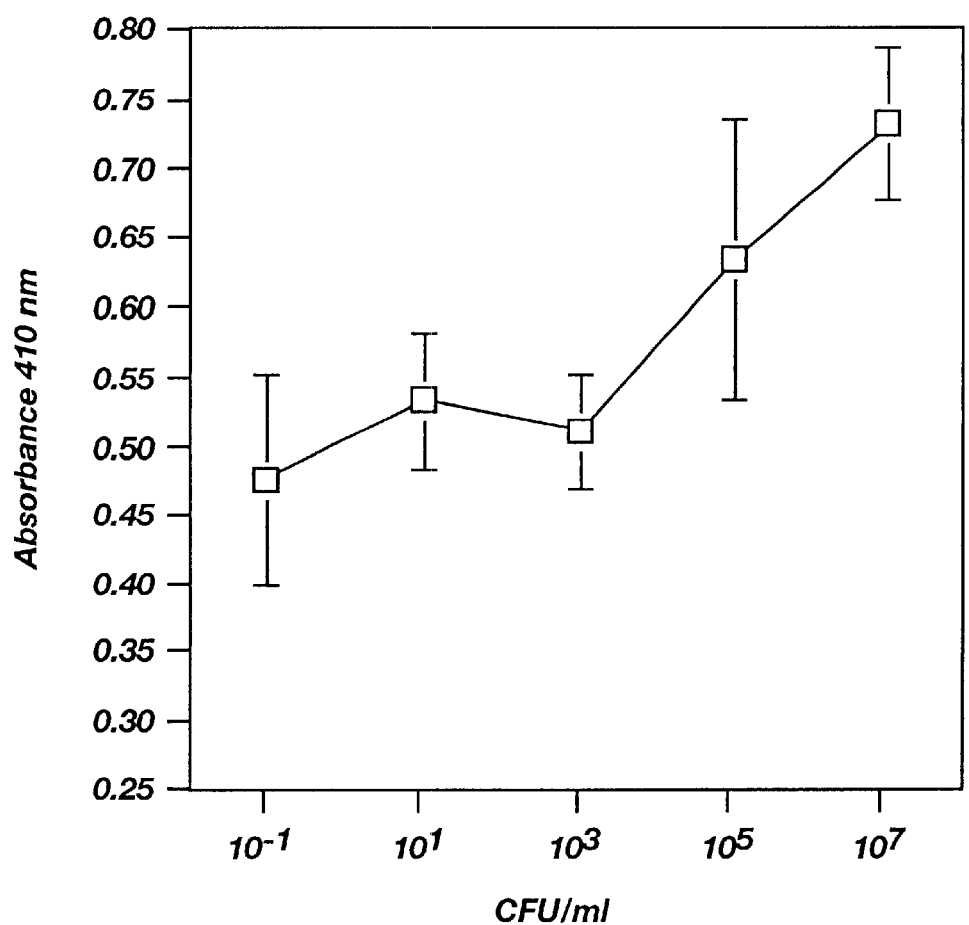
FIG. 5 shows immunoflow (2 L/min) detection of *B. globigii* spores in 0.1 M phosphate buffer (pH 7.2, $R^2 = 0.9$; slope=0.03).
Figure 6:
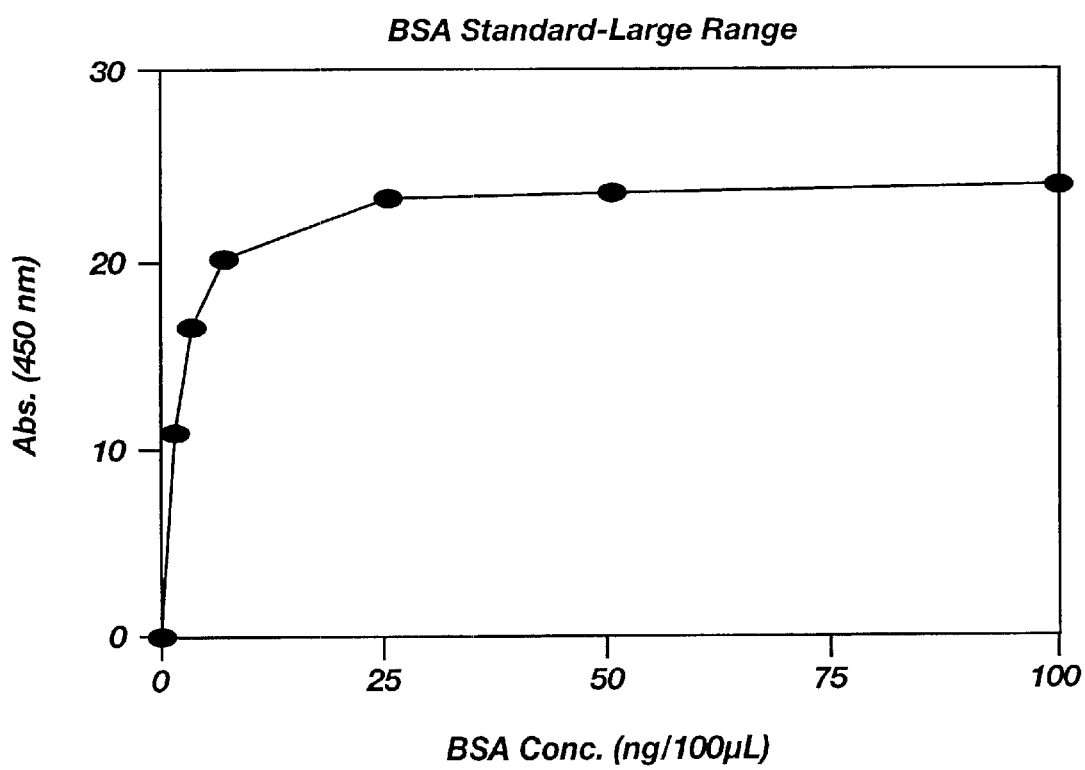
FIG. 6 shows a bovine serum albumin (BSA) standard curve at the range of 1.5–100 ng/μl; each point is the average absorbance (450 nm) in triplicate, and PBST (0.2% Tween 20) was the blocking reagent to block the nonspecific binding sites.
Figure 7:
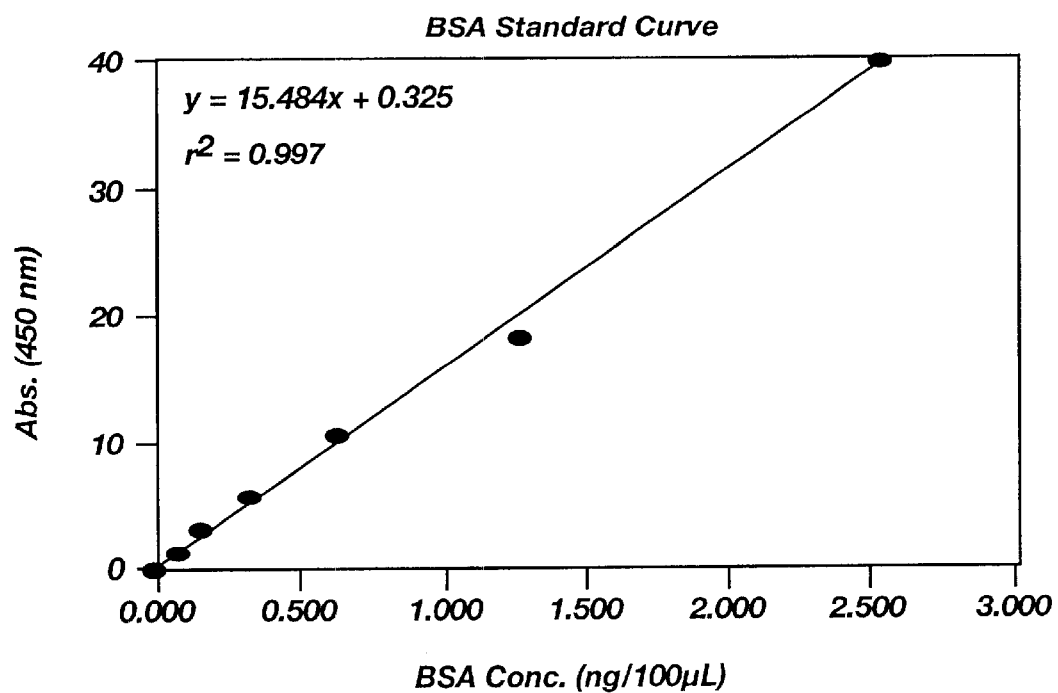
FIG. 7 shows a BSA standard curve at the range of 0.075–2.5 ng/μl; each point is the average absorbance (450 nm) in triplicate; PBST (0.2% Tween 20) was the blocking reagent.

While detection of spores was achieved with immunomagnetic beads, it was believed that sensitivity and efficiency could be improved by using a fluidized bed capture system. Hence, the capture step was fluidized by immobilizing antibodies onto larger beads ranging is size from 1–7 mm. Use of a fluidized bed module (FIG. 4) further increased the sensitivity of the assay to less than a single cell per ml of liquid and allowed the assay to be done without pre-incubation and to obtain a finished result within 30 min in all the samples tested (FIG. 5). FIG. 4 shows a schematic representation of an illustrative module 30 comprising a housing 34 having an inlet opening 38 for flow of a liquid medium to be tested into the module. A plate 46 having holes therein to permit flow of the liquid through the module is placed with the plane of the plate generally perpendicular to the direction of flow of the liquid. The beads 50 are placed upstream of the plate. Arrow 54 shows the direction of flow of liquid through the module. The size of the holes in the plate is selected to be smaller than the size of the beads such that the beads cannot pass through the outflow opening 42. In an illustrative embodiment of the module, the holes in the plate were 3 mm in diameter, and the beads were 7 mm in diameter. The housing and plate should be constructed of materials, such as stainless steel and high durability plastics, having high durability and compatibility with liquids of various types.

EXAMPLE 15

In this example, 0.1 M phosphate buffer, pH 7.2, containing various concentrations of *B. globigii* spores was passed through an immunoflow module containing 7 mm ceramic beads having anti-*B. globigii* antibodies conjugated thereto according to the procedure of Example 6. The buffer was pumped through the module at 2 L/min. After capture of the spores, all of the beads were removed from the module, and a solid phase ELISA using biotinylated anti-*B. globigii* antibodies to amplify the signal was performed according to the procedure of Blake & Weimer, supra. The signal was read at 410 nm in a Biospec 1601 (Shimadzu Scientific Corp., Columbia, Md.) and compared to a standard curve. FIG. 5 shows that spores could easily be detected at concentration of less than 1 cfu/ml.

In a companion experiment, the following foods were tested for the presence of *B. globigii* spores by immunoflow capture: raw whole milk, skim milk, raw hamburger, canned green beans, canned corn, canned peas, canned carrots, canned mixed vegetables, canned spinach, beer, fermented sausage, Vienna sausage, raw chicken, canned chicken, canned pork and beans, canned kidney beans, fresh sliced mushrooms, and canned tomato sauce. Fluid products were tested without modification. Other products were dissolved or suspended at 1 g/ml. Fifty ml of product was pumped through the module at a rate of 2.5 L/min. Bound spores were quantitated using fluorescence detection as described above. *B. globigii* spores were detected in each of these foods at a concentration of 1 spore/ml.

This is a significant improvement over prior results and provided a method for increasing the sample size that could be used. Use of immunoflow at 2–4 L/min allowed detection in less time and in the presence of fat or protein that interfered with immunomagnetic detection and some foods. A characteristic dip at $10^3$ spores/ml was found, which is commonly observed. The cause for this deviation is unknown but is linked to the lower flow rate used, since this dip is not noticeable at flow rates >4L/min. The dynamic range is at least nine decades, suggesting this module will not easily be overloaded in the field.

EXAMPLE 16

In this example, the procedure of Example 15 was carried out except that river water (pH 8.5) with added *B. globigii* spores ($10^3$ spores/ml) was pumped through the module at a flow rate from 1 to 4 L/min for times ranging from 1 to 180 minutes. Detection and spore capture increased as the flow rate increased, with the maximum detection at 15 minutes and a flow rate of 4 L/min. Detection decreased as the flow rate decreased and as the flow time increased.

These data suggest a complex interaction between the capture surface and the spore is occurring, but that it is not matrix dependent. Similar results were observed with detection of *B. globigii* spores in PBS and penicillin in milk at 114 L/min. Additionally, the results obtained with penicillin detection suggests that the range of flow rates for capture and detection is large, at least 1–114 L/min.

To demonstrate the use of immunoflow with small protein targets, BSA detection was done using immunoflow with 5 mm glass beads modified with dextran and anti-BSA antibodies and a flow rate of 2 L/min. The assay detected BSA over a broad range (FIG. 6), and had a lower detection limit of at least 0.075 ng/ml without the avidin/biotin complex for amplification (FIG. 7). These data confirm the use of immunoflow detection for use with chemicals (penicillin), small proteins (BSA), and microbes (Bacillus spores) at flow rates varying from 1–114 L/min.

I claim:

1. A composition represented by the formula B—X—A wherein B is a solid substrate in the form of a bead, A is an antibody, and X is a spacer comprising poly(threonine).

2. The composition of claim 1 wherein said bead is composed of a material selected from the group consisting of glass and ceramics.

3. The composition of claim 2, wherein said bead has a diameter in the range of about 1 to 7 millimeters (mm).

4. The composition of claim 1 wherein said antibody has a specific affinity for binding a microorganism or propagule thereof.

* * * * *